United States Patent [19]

Hool et al.

[11] 3,982,022

[45] Sept. 21, 1976

[54] SYNERGISTIC COMPOSITION FOR THE CONTROL OF BACTERIA

[75] Inventors: Gerhard Hool, Basel, Switzerland; Hans Kundig, Johannesburg, South Africa

[73] Assignee: Ciba-Geigy Corporation, Ardsley, N.Y.

[22] Filed: May 15, 1974

[21] Appl. No.: 469,993

Related U.S. Application Data

[62] Division of Ser. No. 146,854, May 25, 1971, abandoned.

[30] Foreign Application Priority Data

May 26, 1970 Belgium .................................. 89520

[52] U.S. Cl. ............................... 424/341; 424/343; 424/347
[51] Int. Cl.² ..................... A01N 9/24; A61K 31/09
[58] Field of Search ..................... 424/347, 341, 343

[56] References Cited

UNITED STATES PATENTS 3,506,720  4/1970  Model et al. ........................ 424/304

FOREIGN PATENTS OR APPLICATIONS 1,385,825  2/1964  France

OTHER PUBLICATIONS

Merck Index, 7th Ed., (1960), p. 798.
Merck Index, 7th Ed., (1960), p. 792.

*Primary Examiner*—V. D. Turner
*Attorney, Agent, or Firm*—Joseph G. Kolodny; John J. Maitner; Theodore O. Groeger

[57] ABSTRACT

Microorganisms are controlled using combinations of halogenated o-phenoxyphenols and phenoxy or phenalkyl alcohols.

4 Claims, No Drawings

SYNERGISTIC COMPOSITION FOR THE CONTROL OF BACTERIA

This is a division of application Ser. No. 146,854 filed May 25, 1971, now abandoned.

The present invention relates to new compositions for the control of microorganisms. The object of the French Pat. No. 1,385,825 is a process for the control of microorganisms, the process being based on the use of halogenated o-phenoxyphenols of formula I:

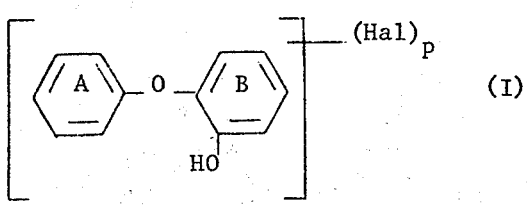

wherein
Hal represents a halogen atom, and
P represents a whole number from 1 to 5, and the rings A and B can carry further substituents.

Furthermore, J. Soc. Cosmetic Chemists 19, 531–549 (1968) deals with antimicrobic active substances and combinations of active substances which are effective both against gram-positive and against gram-negative microorganisms. As being particularly effective are mentioned in this publication compounds of the type phenoxyethanol, which can be substituted or not substituted by halogen. In the last-mentioned case, the compounds are effective only against gram-negative microorganisms.

Each of the two classes of compounds has been found to be non-toxic and not to irritate the skin. The disadvantage of the two classes is mainly their slow germicidal action.

Surprisingly, it has been found that by a combination of compounds of the two above described classes of compounds is obtained, with full retention of the wide range of action, possessed especially by the compounds of the halogenated o-phenoxyphenol type, a very rapid total disinfection and an almost complete destruction of all germs.

The new compositions according to the invention for the control of microorganisms are characterised in that they contain a combination of active substances consisting of a first compound of formula I:

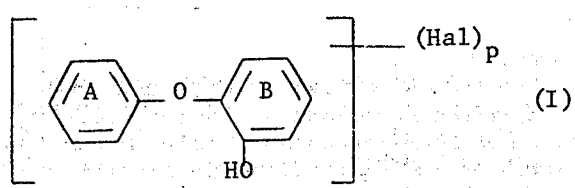

wherein
P represents a whole number from 1 to 5, and
Hal represents a halogen atom, and the benzene nuclei A and B can moreover carry lower, optionally halogenated alkyl groups, lower alkoxy groups, allyl, cyano, amino, or acetyl groups;
or of an O-acyl derivative thereof with respect to the hydroxyl group,
and a second compound of formula II:

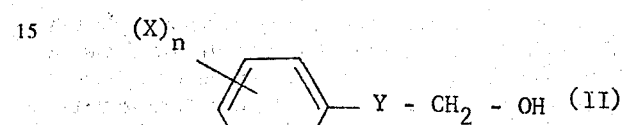

wherein
$n$ represents 0 or a whole number from 1 to 5,
X represents a halogen atom, and
Y represents a radical of the formula —O—CH$_2$— or —CH$_2$— or the direct bond, together with the usual carriers and/or dispersing agents.

Suitable as halogen in the compounds of the general formula I and II are: fluorine, bromine, iodine and, in particular, chlorine; $n$ is preferably 0, 1 or 2.

The lower alkyl and alkoxy groups bound to the benzene nuclei are, preferably, methyl or methoxy groups; halogenated lower alkyl groups are, in particular, trifluoromethyl groups.

In order to obtain a biocidal action comparable with that of the halogenated o-phenoxyphenols of the general formula I, the O-acyl derivatives of these can equally as well be used, these undergoing, under the conditions of application, a partial or complete hydrolysis. For this purpose it is particularly advisable to use esters derived from acetic acid, chloroacetic acid, methyl- or dimethylcarbamic acid, benzoic acid, chlorobenzoic acid, methanesulphonic acid and chloromethanesulphonic acid.

The halogenated o-phenoxyphenols corresponding to formula III, which is restricted with respect to formula I,

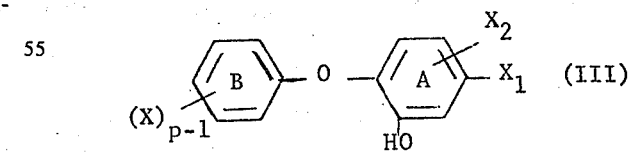

and their O-acyl derivatives, constitute a class of compounds particularly effective against microorganisms.

In formula III $X_1$ represents hydrogen or halogen, $X_2$ represents hydrogen or, if $X_1$ is chlorine, likewise chlorine, X represents halogen, and P represents a positive whole number from 1 – 5 and, in the case where $X_1$ and $X_2$ each represent hydrogen, a positive whole number from 3 – 5.

The total number of halogen atoms contained in the molecule is at most 5, and the benzene nuclei, especially the nucleus B, can also carry alkyl groups optionally halogenated, lower alkoxy groups, allyl, cyano, amino, or acetyl groups.

Of these preferred halogenated o-phenoxyphenols corresponding to the general formula III, two classes of compounds deserve special mention, since they have a particularly good bactericidal action, and are very suitable for the disinfection of washable materials and for the protection thereof against attack by microorganisms. These two classes are the o-phenoxyphenols containing no halogen in the benzene nucleus A and corresponding to the general formula IV:

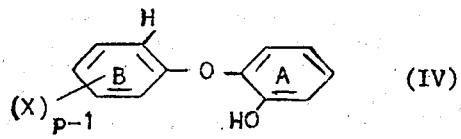

(IV)

wherein

X represents a halogen atom, and

P denotes a positive whole number from 3 – 5, and the o-phenoxyphenols carrying a halogen atom in the benzene nucleus A in para-position to the ether bond, and corresponding to the general formula V

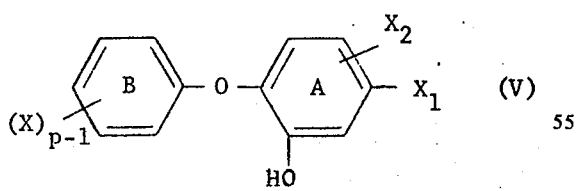

(V)

wherein

X and $X_1$ each represent, independently of each other, a halogen atom, $X_2$ represents hydrogen or, if $X_1$ is chlorine, likewise chlorine, and p represents a positive whole number from 1 to 5.

In the compounds of the general formulae IV and V, the benzene nuclei, especially, however, the benzene nucleus B, can also carry methyl, trifluoromethyl, or methoxy groups.

Likewise of importance are the o-phenoxyphenols (embraced by the general formula I) of the general formula VI:

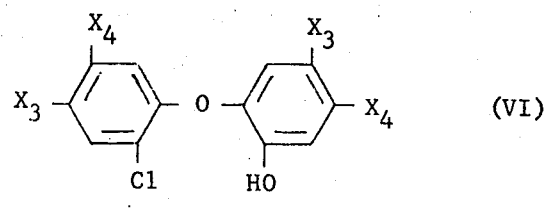

(VI)

wherein $X_3$ represents chlorine, a lower alkyl group, or hydrogen, and $X_4$ represents hydrogen or a lower alkyl group, whereby, however, $X_3$ and $X_4$ cannot simultaneously represent lower alkyl groups.

Particularly preferred of the halogenated o-phenoxyphenols of the general formula V are those of the subgroup of the general formula VII:

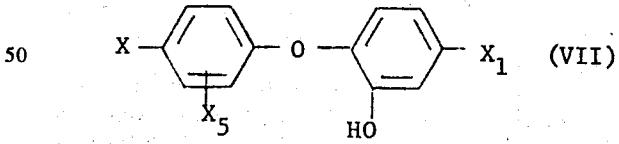

(VII)

wherein

X and $X_1$ each represent a halogen atom, and $X_5$ represents hydrogen or a halogen atom, such as 5-chloro-2-(2,4-dichlorophenoxy)-phenol; and of the compounds of the general formula VI: 4-chloro-2-(2,4-dichlorophenoxy)-phenol.

The compounds of formula I can be produced by various known methods: see, in particular, the French Pat. No. 1,385,825, and also for the compounds of the general formula VI and the last-mentioned compound the German patent application open for public inspection, German Pat. No. 2,005,883, and for the compounds of the general formula VII also the French Pat. No. 1,386,731.

Preferably used compounds of formula II wherein Y represents the group —O—CH₂ are: 2-phenoxyethanol

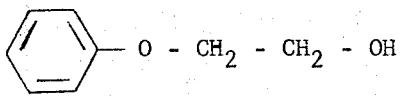

and 2-(p-chlorophenoxy)-ethanol

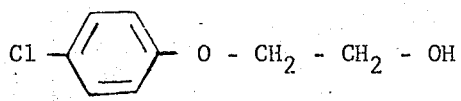

The most important compounds of formula II having the group —CH₂— as the radical Y are: phenethyl alcohol

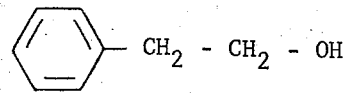

and p-chlorophenethyl alcohol

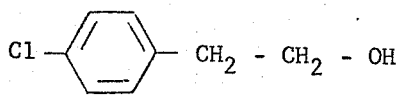

Suitable compounds of formula II wherein Y represents the direct bond are, in particular, monochlorobenzyl alcohols and 2,4-dichlorobenzyl alcohol.

The active substance combinations of the new compositions for the control of microorganisms are distinguished by a low toxicity with respect to warm-blooded animals, and by the absence of an irritation of the skin when used in the concentrations needed in practice. In the first place they are effective against bacteria. The bactericidal action extends both to gram-positive bacterial flora and to gram-negative bacterial flora, e.g. to staphylococcal such as *Staphylococcus aureus* SG 511, and especially to coliforms such as *Escherichia coli*, as well as to other gram-negative organisms such as *Psuedomonas aeruginosa*.

The antimicrobic compositions according to the invention containing the above defined combinations of active substances can be in the form of solutions or dispersions. The active substance combinations are soluble in dilute sodium hydroxide solution of potassium hydroxide solution, and in practically all organic solvents. They are preferably used in an aqueous medium. They can be applied in the most diverse ways to control microorganisms, particularly bacteria, and for the protection of organic materials and objects against infestation by microorganisms.

The relative concentrations of the two antimicrobic constituents of the compositions according to the invention depend on the intended application of the compositions concerned. Since, however, the synergism of the antimicrobic compositions according to the invention lies in the surprising speed at which is attained an almost complete destruction of the germs, the respective concentration limits are fairly narrow, and the concentrations are, in general, as high as if the constituents are used separately as active substances. The compositions according to the invention can be used in all cases where normally compositions are used containing the one or the other constituent as the sole active substance. Mention is made here of agents for the cleansing and disinfection of the hands, especially for surgeons' hands. Likewise mentioned are cleansing agents and disinfectants for textiles, floors and walls, as well as for hospital equipment and instruments.

It is possible to incorporate the antimicrobic active substance combinations into antiseptic shampoos, antimicrobic creams, ointments, powders, washing and rinsing agents, as well as into disinfectants for industrial application in agricultural concerns, in the food industry, in breweries and laundries, and into agents for general disinfection in overcrowded living quarters, and to obtain in this manner compositions according to the invention.

The antimicrobic active substance combinations are also used for the preservation of various cosmetic and pharmaceutical products. For example, they can, for this purpose, be incorporated into hand and face creams, or into oils which can be applied to the body. The antimicrobic active substance combinations, especially in the form of concentrated solutions, can be added to all types of lubricating oils, hydraulic oils, and to oils used for other purposes in industry, particularly to drilling oils, as well as to light and heavy liquid fuels, for the preservation thereof.

Of the above stated types of compositions according to the invention for the control of microorganisms those types are of particular importance which are usable for the disinfection of healthy skin, especially of the hands, for the treatment of microbic skin infections, and for the disinfection of wounds, and which thus contain carriers and/or dispersing agents which are pharmaceutically acceptable for external application. Hand disinfectants which are first rubbed into the hands, then gradually diluted with water and finally washed off, with the exception of active substances and fatty substances contained in the disinfectants, contain, for example, as main constituent at least one of each of the two antimicrobic active substance types, a hydroxy compound which is water-miscible or at least easily soluble in water, such as, e.g. glycerin, propylene glycol, ethanol and/or isopropanol, at least one surface-active substance such as, e.g. sodium-lauryl sulphate or sodium lauroyl sarcosinate, as well as, optionally, wool fat or chemically modified wool fat, e.g. etherified and/or acylated wool fat, for the improvement of the cosmetic properties, or as skin-care additives, aromatics and further additives, as well as water. For care of the skin in the case of repeated application, it is of advantage to maintain the pH-value of the aforementioned and other aqueous preparations in a slightly acid range, e.g. between 5.5 and 6.5, by the addition of weak organic acids such as, e.g. citric acid, lactic acid, or tartaric acid. Anhydrous ointments contain as a foundation, e.g. soft paraffin (vaseline) and/or wool fat; and aqueous ointments (creams) contain, besides the stated foundation substances, e.g. also appreciable amounts of higher fatty alcohols and/or waxes (fatty acid esters of fatty alcohols), as well as surface-active substances as emulsifiers, and water. These preparations are used, in particular, for the prevention and treatment of infectious skin infections, and for the treatment of wounds. Liquid preparations, such as suspensions and solutions, are particularly suitable for the disinfection of skin and wounds. Suspensions contain besides the active substances, e.g. small amounts of water-soluble hydroxy compounds such as glycerin, viscosity-raising substances such as tragacanth and/or hydroxyethyl cellulose, optionally, surface-active substances and a larger proportion of water, whereas in solutions the proportion of mono- and/or polyhydroxy compounds, e.g. ethanol, isopropanol, propylene glycol, glycerin, liquid polyethylene glycol, or mixtures thereof, is high in comparison with the water content. With the use of these solvents, there need be no water present.

A further suitable application form, especially for the treatment of skin infections and for the disinfection of wounds, are powders. Suitable carriers for these are, e.g. starches such as rice starch, which, optionally, can be made specifically lighter, e.g. by the addition of highly-dispersed silicic acid, or heavier by the addition of talcum.

The active substance concentration in the aforementioned compositions is, e.g. between 0.1% and 5% of each constituent, preferably 1 to 3% of halogen-substituted o-phenoxyphenol of the general formula I, and 1 to 5% of a compound of the general formula II, so that the preferred proportions of the constituents I and II are between 3:1 and 1:5.

In the following test examples, the final concentrations are in some cases considerably below the aforementioned concentrations, whereby, in particular to the in vitro tests, the concentration of halogenated o-phenoxyphenol is, in comparison with that of the compound of the general formula II, appreciable lower. As is known, in the case of most antimicrobic active substances which are in vitro highly effective, the required concentrations in the practical application of these antimicrobic active substances, especially in the disinfection of wounds on account of the lowering of effectiveness as a result of blood and/or serum, are substantially higher than the concentrations which would be effective in in vitro tests. This applies also to the halogenated o-phenoxyphenols of the general formula I, whilst the activity of the compounds of the general formula II, which in themselves are effective only in fairly high dosages, is relatively only slightly reduced under practical conditions. Thus, concentrations of both active substances are advisable for practical application which lie considerably nearer together than those deduced from the in vitro tests and from tests made on intact skin.

In all application forms, whether they be intended for technical, cosmetic, hygienic, or medicinal fields of application, combinations of at least one active substance each of formula I and formula II can be present as the sole active substances, or they can be combined with other known antimicrobic active substances, especially with antibacterial and/or fungicidal or antimycotic active substances, e.g. for the widening of the sphere of action. They can be combined, e.g. with halogenated salicyclic acid alkyl amides and -anilides, with halogenated diphenylureas, with polychlorohydroxydiphenylmethanes, or with halogen-dihydroxydisulphides. It is possible, particularly in medicinal preparations, to also add active substances for the treatment of side effects of infections, e.g. locally administrable corticosteroids, such as hydrocortisone of flumethasone-pivalate, for the treatment of simultaneous inflammations. On the other hand, the active substance combinations can also be added to agents for the treatment of other skin diseases such as, e.g. eczema, acne or psoriasis, for the prevention of secondary infections. Optionally, it is also possible to use carriers having pharmacologically favourable inherent effects, such as, e.g. sulphur as a powder base, or zinc stearate as a constituent of ointment foundations.

A series of test examples A to D is given in the following, followed by some examples concerning compositions according to the invention; the examples, however, do not in any way limit the scope of the invention.

EXAMPLES A

Tests on hands artificially contaminated

The method utilised for these tests is described below. The microorganisms tested are:
*Escherichia coli*
*Pseudomonas aeruginosa*

A disinfectant solution was used having an active substance concentration sufficient to destroy the germs within a period of 3 minutes (bactericidal effect). The tips of the fingers of hands not disinfected beforehand were contaminated, with the aid of a 1-ml pipette, with one drop per finger of a culture of microorganisms, the culture having been incubated beforehand in a bouillon for 16–24 hours. Thus, 5 drops were used for each hand. The results of these disinfection tests are closely related to the number of microorganisms present in the culture used. It is therefore necessary to determine the number of germs in the culture; this number must not be below $10^8$ organisms per milliliter. The applied drops are dispersed uniformly over the tips of the fingers by rubbing with the thumb for about one minute. Following this, the hands are plunged into two liters of the disinfectant solution being examined, and are held there for 1 to 5 minutes. The disinfectant solution is maintained at room temperature.

After this period of disinfection, the hands are rinsed with lukewarm water (35°C) for 10 seconds. The bulk of this rinsing water is removed on shaking the hands. In order to determine the possibility of survival of microorganisms, the tips of the fingers are immediately introduced into a dish containing 10 ml of a normal bouillon culture, and 20% of deactivating serum is added. The tips of the fingers are rubbed on the bottom of the dish for 1 minute. With the aid of a pipette, 0.1 ml of this bouillon is withdrawn and deposited on the surface of a petri dish containing End-Agar, the bouillon being then evenly distributed over the whole surface. After a 48 hour incubation at 37°C of the nutritive medium thus innoculated, a count is made of the colonies which have developed. The results are given in a table containing various columns corresponding to the determined number of microorganisms. Identification is as follows.

hands with 0 germs; 1 – 10; 11 – 50; 51 – 100; 101 – 200; and with more than 200 germs.

EXAMPLE A 1

Microorganism: Pseudomonas aeruginosa
Number of microorganisms in the bouillon culture 5 $\times 10^8$/ml

| Active substance | Final concentration % | Immersion time in minutes | No. of hands | \multicolumn{6}{c}{Number of hands after desinfection on which the number of germs is} |
| --- | --- | --- | --- | --- | --- | --- | --- | --- | --- |
| | | | | 0 | 1–10 | 11–50 | 51–100 | 101–200 | more than 200 |
| 2-(p-chlorophenoxy)-ethanol | 0.5 | 5 | 12 | — | 2 | 6 | 1 | 2 | 1 |
| 5-chloro-2-(2,4-dichlorophenoxy)-phenol | 0.5 | 5 | 10 | — | — | — | 4 | 2 | 4 |
| 2-(p-chlorophenoxy)-ethanol + 5-chloro-2-(2,4-dichlorophenoxy)-phenol | 0.25 0.1 | 2 | 14 | 4 | 8 | 2 | — | — | — |

This table clearly shows the existence of the synergistic action of the new composition.

It is seen that with an immersion time of 2 minutes for the composition 4 hands are counted on which no further germs are found, whereas the results obtained with each of the constituents used alone are clearly inferior, even with a disinfection time of 5 minutes.

EXAMPLE A 2

Microorganism: Escherichia coli
Number of microorganisms in the bouillon culture $8.5 \times 10^8$/ml rubbed for 1 minute on the bottom of a petri dish containing 10 ml of a bouillon culture.

The number of microorganisms introduced into the bouillon is then determined on culture media. With the contaminated bouillon is prepared a dilution series (up to $1/10^5$). To 1 ml of the initial bouillon and to each of the dilutions are added 12 ml of the hot liquid culture medium (45°C). The mixture thus obtained are placed in the sterilised petri dishes. After two days' incubation of the cultures at 37°C, the colonies are counted.

The main test is carried out along similar lines. After rinsing of the hands with lukewarm water followed by

| Active Substance | Final concentration % | Immersion time in minutes | No. of hands | \multicolumn{6}{c}{Number of hands after disinfection on which the number of germs is} |
| --- | --- | --- | --- | --- | --- | --- | --- | --- | --- |
| | | | | 0 | 1–10 | 11–50 | 51–100 | 101–200 | more than 200 |
| 2-(p-chlorophenoxy)-ethanol | 0.125 | 5 | 8 | 1 | 3 | 3 | 1 | — | — |
| 5-chloro-2-(2,4-dichlorophenoxy)-phenol | 0.001 | 5 | 8 | — | — | 1 | 4 | 2 | 1 |
| 5-chloro-2-(2,4-dichlorophenoxy)-phenol +2-(p-chlorophenoxy)-ethanol | 0.001 0.0625 | 3 | 12 | 8 | 3 | 1 | — | — | — |

With each of the compounds used alone, the obtained results are clearly less satisfactory than with the mixture, which demonstrates very clearly the synergism in the speed of antimicrobic action and the reduced concentration of one of the compounds. Already at the end of 3 minutes of contact eight hands are counted on which no further germs are detected.

EXAMPLE B

Tests with regard to disinfection of the skin

Method

Hands not artificially contaminated are used as models.

Before commencement of the test, the persons concerned wash their hands for 3 minutes with lukewarm water (35°C), using normal soap (without bacteriostatic agent), and a previously sterilised hand brush.

The 'residue' of microorganisms is then determined as follows: The finger of the right and left hand are drying, the hands are immersed into two liters of the disinfectant solution being tested. Use of the hand brush is restricted to a cleaning of the nails.

The duration of the disinfection treatment never exceeds 5 minutes. After this operation, the hands are rinsed with water for one minute. The tips of the fingers of the left and the right hand are rubbed during one minute on the bottom of the sterilised petri dishes, each containing 10 ml of the bouillon culture (with 20% of the deactivating serum).

As comparison disinfectant solution is used a solution with 60% by volume of propyl alcohol. Compounds tested:

1. 2-phenoxyethanol 1.5% during 5 minutes,
2. 5-chloro-2-(2,4-dichlorophenoxy)-phenol 0.25% during 5 minutes,
3. 2-phenoxyethanol 1.00% + 5-chloro-2-(2,4-dichlorophenoxy)-phenol 0.125% during 3 minutes,
4. n-propyl alcohol 60% vol. during 5 minutes.

HAND DISINFECTION TESTS

| | Compound tested | | | Comparison tests | | |
|---|---|---|---|---|---|---|
| | 5-Chloro-2-(2,4-dichlorophenoxy)-phenol 0.25% Number of microorganisms | | | n-Propyl alcohol (60%) Number of microorganisms | | |
| Hands of persons tested | Before disinfection | After disinfection (5 min) | % Reduction in number of microorganisms | Before disinfection | After disinfection (5 min) | % Reduction in number of microorganisms |
| 1) right | 5.600 | 200 | 96.43 | 6.200 | 4 | 99.9 |
| left | 6.600 | 600 | 90.91 | 6.000 | 12 | 99.8 |
| 2) right | 3.400 | 800 | 76.47 | 4.400 | 6 | 99.87 |
| left | 4.600 | 400 | 91.30 | 5.200 | 10 | 99.8 |
| 3) right | 6.400 | 1000 | 84.37 | 5.800 | 15 | 99.7 |
| left | 7.600 | 1400 | 81.58 | 6.800 | 5 | 99.9 |
| 4) right | 2.800 | 400 | 85.71 | 4.400 | 10 | 99.73 |
| left | 3.200 | 150 | 95.31 | 5.600 | 4 | 99.9 |
| 5) right | 6.400 | 800 | 87.50 | 4.600 | 8 | 99.8 |
| left | 4.800 | 1200 | 75.00 | 3.800 | 12 | 99.7 |
| mean percentage | | | 86.45 | | | 99.81 |

HAND DISINFECTION TESTS

| | Compound tested | | | Comparison tests | | |
|---|---|---|---|---|---|---|
| | 2-Phenoxy-ethanol 1.5% (dispersed in H₂O) Number of microorganisms | | | n-Propyl alcohol (60%) Number of microorganisms | | |
| Hands of persons tested | Before disinfection | After disinfection (5 min) | % Reduction in number of microorganisms | Before disinfection | After disinfection (5 min) | % Reduction in number of microorganisms |
| 1) right | 6.600 | 350 | 94.7 | 5.600 | 14 | 99.75 |
| left | 4.800 | 700 | 85.4 | 5.200 | 16 | 99.7 |
| 2) right | 7.200 | 1,200 | 83.3 | 8.800 | 180 | 97.9 |
| left | 8.400 | 900 | 89.3 | 8.200 | 150 | 98.2 |
| 3) right | 5.400 | 150 | 97.3 | 4.200 | 8 | 99.8 |
| left | 6.200 | 80 | 98.7 | 5.600 | 24 | 99.6 |
| 4) right | 3.600 | 800 | 77.8 (?) | 4.400 | 15 | 99.65 |
| left | 4.200 | 450 | 89.3 | 5.200 | 5 | 99.9 |
| 5) right | 3.800 | 160 | 95.8 | 2.800 | 60 | 97.8 |
| left | 3.400 | 200 | 94.4 | 3.400 | 20 | 99.4 |
| mean percentage | | | 90.60 | | | 99.17 |

HAND DISINFECTION TESTS

| | Compound tested | | | Comparison tests | | |
|---|---|---|---|---|---|---|
| | 2-Phenoxy-ethanol 1% + 5-Chloro-2-(2,4-dichlorophenoxy)-phenol 0.125% Number of microorganisms | | | n-Propyl alcohol (60%) Number of microorganisms | | |
| Hands of persons tests | Before disinfection | After disinfection (3 min) | % Reduction in number of microorganisms | Before disinfection | After disinfection (5 min) | % Reduction in the number of microorganisms |
| 1) right | 5.400 | 14 | 99.7 | 6.200 | 24 | 99.6 |
| left | 4.600 | 6 | 99.87 | 5.000 | 15 | 99.7 |
| 2) right | 2.800 | 6 | 99.8 | 3.400 | 14 | 99.6 |
| left | 4.000 | 2 | 99.9 | 3.800 | 12 | 99.7 |
| 3) right | 8.400 | 4 | 99.9 | 7.200 | 120 | 98.3 |
| left | 8.000 | 10 | 99.88 | 7.800 | 160 | 97.95 |
| 4) right | 3.800 | 30 | 99.2 | 4.600 | 20 | 99.56 |
| left | 3.200 | 12 | 99.6 | 5.400 | 26 | 99.5 |
| 5) right | 6.200 | 12 | 99.8 | 5.800 | 6 | 99.9 |
| left | 6.800 | 10 | 99.85 | 6.400 | 10 | 99.84 |
| mean percentage | | | 99.75 | | | 99.37 |

Discussion and conclusion

The mixture of the two active constituents exhibits a genuine synergistic action. Special attention is to be paid to the time interval in which the mixture of 5-chloro-2-(2,4-dichlorophenoxy)-phenol and 2-phenoxy-ethanol is able to develop a total disinfecting action against the microorganisms which can be present on the skin. Further tests were carried out whereby the phenoxy-ethanol was replaced by p-chloro-phenoxy-ethanol.

EXAMPLE C

Applied method

The method used is analogous to that described by Boehm in J. Soc. Cosmetic Chemists 19, 531–549 (1968).

Principle

Test tubes containing the standardised reaction mixtures are inoculated with one of the microorganisms. Particular attention is paid to maintaining constant the amount of microorganisms to be introduced into the test tubes. After accurately defined contact times, sufficient amounts of mixture are taken to determine, by application of this amount of mixture to a dish with nutritive-Agar and counting after incubation, the number of germs surviving.

Definitions

1. Reaction mixtures

Reaction mixtures are prepared consisting principally of a bouillon culture. The reaction mixtures also contain the two constituents: 5-chloro-2-(2,4-dichlorophenoxy)-phenol and 2-phenoxy-ethanol or p-chloro-2-phenoxy-ethanol, of which the concentrations are given in the various tables. The bouillon culture is, at the same time, solvent for the compound of the phenoxy-ethanol type, whilst 1% of 2-methoxy-ethanol serves as solvent for the 5-chloro-2-(2,4-dichlorophenoxy)-phenol.

2. Contact time

The contact times for the series of examples are: 3 minutes, 30 minutes, 5 hours, and 24 hours.

3. Microorganisms

The main types of microorganisms tested are:
*Pseudomonas aeruginosa* ATCC 15 442
*Staphylococcus aureus* SG 511
*Esherichia coli* ATCC 4352

EXAMPLE C 1

Using the method described above, the action of antimicrobic compositions containing 5-chloro-2-(2,4-dichlorophenoxy)-phenol and 2-phenoxy-ethanol on the Staphylococcus aureus SG 511 was tested. Two reference compositions each containing only one of the above mentioned constituents were tested in order to demonstrate the synergetic effect.

Table I

| Microorganism tested: Staphylococcus aureus SG 511 | | | | | |
|---|---|---|---|---|---|
| Tested active substances: 5-chloro-2-(2,4-dichlorophenoxy)-phenol, ppm | | Number of germs remaining after an exposure to the reaction mixture of: | | | |
| + 2-phenoxy-ethanol ppm | | 3 min. | 30 min. | 5 h | 24 h |
| — | — | $1.10^4$ | $2.10^4$ | $3.10^4$ | $>10^5$ |
| 0 | 5'000 | $1.10^4$ | $2.10^4$ | $2.10^4$ | $8.10^3$ |
| 0 | 10'000 | $1.10^4$ | $2.10^4$ | $8.10^3$ | $2.10^1$ |
| 3 | 0 | $1.10^4$ | $2.10^4$ | $3.10^3$ | $5.10^1$ |
| 10 | 0 | $1.10^4$ | $2.10^2$ | 0 | 0 |
| 10 | 5'000 | $8.10^1$ | 1 | 0 | 0 |
| 1 | 10'000 | $2.10^4$ | $1.10^4$ | 0 | 0 |
| 3 | 10'000 | $2.10^4$ | $3.10^3$ | 0 | 0 |
| 10 | 10'000 | 0 | 0 | 0 | 0 |

The results given in Table 1 clearly prove that the compositions containing 2-phenoxy-ethanol and 5-chloro-2-(2,4-dichlorophenoxy)-phenol display a positive synergetic effect which is reflected in the speed of the antimicrobic action, or in the reduction of the required concentration.

EXAMPLE C 2

Antimicrobic compositions according to the invention were tested likewise with application of the previously described method.

Table II

| Microorganism tested: Escherichia coli ATCC 4352 | | | | | |
|---|---|---|---|---|---|
| Tested active substances: 5-chloro-2-(2,4-dichlorophenoxy)-phenol, ppm | | Number of germs remaining after an exposure to the reaction mixture of: | | | |
| + 2-phenoxy-ethanol, ppm | | 3 min. | 30 min. | 5 h | 24 h |
| 0 | 0 | $10^4$ | $5.10^3$ | $2.10^4$ | $10^5$ |
| 0 | 10'000 | $4.10^3$ | $4.10^3$ | 0 | 0 |
| 10 | 0 | $1.10^4$ | $4.10^2$ | $5.10^1$ | 2 |
| 10 | 5'000 | $4.10^2$ | 0 | 0 | 0 |
| 3 | 10'000 | $9.10^2$ | 0 | 0 | 0 |
| 10 | 10'000 | 0 | 0 | 0 | 0 |

These results show that mixtures of: 10 ppm of 2-(2,4-dichlorophenoxy)-phenol + 5000 ppm of 2-phenoxyethanol; 3 ppm of 5-chloro-2-(2,4-dichlorophenoxy)phenol + 10,000 ppm of 2-phenoxy-ethanol display a very rapid bactericidal activity.

EXAMPLE C 3

The microorganism tested in the Pseudomonas aeruginosa ATCC 15442. According to the results in Table III, the mixtures based on 10,000 ppm of 2-phenoxyethanol and 100 ppm and 300 ppm, respectively, of 5-chloro-2-(2,4-dichlorophenoxy)-phenol exhibit the same synergetic activity against this microorganism as against those microorganisms previously tested.

Table III

| Compositions based on: 5-chloro-2-(2,4-dichlorophenoxy)-phenol + 2-phenyl-ethanol. | | | | | |
|---|---|---|---|---|---|
| Microorganism tested: Pseudomonas aeruginosa ATCC 15442. | | | | | |
| Tested active substances: 5-chloro-2-(2,4-dichlorophenoxy)-phenol, ppm | | Number of germs remaining after an exposure to the reaction mixture of: | | | |
| + 2-phenoxy-ethanol, ppm | | 3 min | 30 min | 5 h | 24 h |
| 0 | 5'000 | + | $2.10^4$ | $4.10^3$ | $3.10^3$ |
| 0 | 10'000 | $2.10^4$ | $8.10^3$ | 0 | 0 |
| 30 | 0 | + | + | + | + |
| 100 | 0 | + | + | + | + |
| 300 | 0 | + | + | + | + |
| 10 | 10'000 | + | $3.10^3$ | 0 | 0 |
| 30 | 10'000 | + | $10^3$ | 0 | 0 |
| 100 | 10'000 | $2.10^3$ | 0 | 0 | 0 |
| 300 | 10'000 | 0 | 0 | 0 | 0 |

Note: $+ = >10^5$

EXAMPLE C 4

The same synergetic effect is observed if, in the mixtures, 2-phenoxy-ethanol is replaced by 2-(p-chlorophenoxy)-ethanol.

Table IV

| Mixture of 5-chloro-2-(2,4-dichlorophenoxy)-phenol and 2-(p-chlorophenoxy)-ethanol. | | | | | |
|---|---|---|---|---|---|
| Microorganism tested: Pseudomonas aeruginosa ATCC 15442 | | | | | |
| Tested active substances: 5-chloro-2-(2,4-dichlorophenoxy)-phenol, ppm | | Number of germs remaining after an exposure to the reaction mixture of: | | | |
| + 2-phenoxy-ethanol, ppm | | 3 min | 3 h | 24 h | 48 h |
| 300 | 0 | $10^4$ | $10^4$ | $>10^5$ | $>10^5$ |
| 0 | 1000 | $10^4$ | $10^4$ | $>10^5$ | $>10^5$ |
| 0 | 3000 | $10^3$ | 0 | 0 | 0 |
| 0 | 3000 | $3.10^1$ | 0 | 0 | 0 |
| 10 | 3000 | 3 | 0 | 0 | 0 |
| 30 | 3000 | 0 | 0 | 0 | 0 |

EXAMPLES D

Method

Pseudomonas aeruginosa NCTC 1999 are cultured in a bouillon prepared from 0.5% of yeast extract and 1% of Trypton (Difco) in 0.5% aqueous sodium chloride solution, the operation being performed at 37°C for about 4 hours in an apparatus producing rotary and shaking motions, until the germ count attains ca. $10^9$/ml. The bouillon is then replaced, by repeated centrifuging of the suspension, decanting of the overlying solution and refilling, by 0.85% aqueous sodium chloride solution. This suspension is diluted 100-fold (0.2 ml to 20 ml) at room temperature with the active substance solutions (see below). After this point of time ("0 minutes"), 0.5 ml samples are taken from the thus obtained test mixtures at the minute intervals given in the table, the samples being transferred immediately into adequate amounts of the solution of 1% Tween 80 (polyoxyethylene derivative of sorbitan-monooleate) serving as diluting medium. The antibacterial activity of the test substances is terminated as a result of the dilution and the content of Tween 80. At the latest at the end of the experiment, 0.05 ml of each dilution are applied to serum agar plates (10% serum content) and incubated for about 16 hours at 30°C. The developed bacteria colonies are subsequently counted.

For the preparation of the solution with phenethyl alcohol alone, this is first mixed with the same amount of ethanol, and the mixture then dissolved in an adequate amount of 0.85% aqueous sodium chloride solution. An ethanolic solution as concentrated as possible is firstly prepared of p-chlorophenethyl alcohol, and this solution is thereupon mixed with an adequate amount amount of an 0.85% sodium chloride solution. For the preparation of combined solutions of both active substance types, 5-chloro-2-(2,4-dichlorophenoxy)phenol is first added to the araliphatic alcohol, the procedure being then identical to that given above.

EXAMPLE D 1

Combination of 5-chloro-2-(2,4-dichlorophenoxy)-phenol: AS I with phenethyl alcohol = AS II.

The determined number of bacteria colonies in 0.05 ml is given in Table V.

| Taking of sample after . . . minutes (duration of action) | Bacteria colonies in 0.05 ml after action of: | | |
|---|---|---|---|
| | no active substances[1] | 5000 ppm AS II | 5 ppm AS I 5000 ppm AS II |
| 1 | 96 × $10^3$ 119 | — | 98 × $10^3$ 108 |
| 2 | — | 115 × $10^3$ 105 | 105 × $10^3$ 76 |
| 3 | — | — | 70 × $10^2$ 103 |
| 5 | — | 94 × $10^3$ 83 | 5 × $10^1$ 12 |
| 7 | — | — | 0 |
| 10 | — | 48 × $10^3$ 50 | 0 |
| 20 | — | 10 × $10^3$ 10 | 0 |
| 40 | — | 27 × $10^2$ 28 | 0 |
| 60 | — | — | 0 |
| 80 | — | 0 | 0 |
| 120 | 111 × $10^3$ 87 | 0 | 0 |

[1]Control test with an 0.85% aqueous sodium chloride solution containing 1% of ethanol.

5-Chloro-2-(2,4-dichlorophenoxy)-phenol alone is ineffective in the concentration of 5 ppm used in the combination test. Nevertheless, the combination produces a ca. 6–8 times more rapid destruction than phenethyl alcohol alone, from which is clearly shown the synegistic action of the two constituents.

EXAMPLE D 2

Combination of 5-chloro-2-(2,4-dichlorophenoxy)-phenol = AS I with p-chlorophenethyl alcohol = AS III.

The determined number of bacteria colonies in 0.05 ml is given in Table VI.

| Taking of sample after . . . minutes (duration of action) | Bacteria colonies in 0.05 ml after action of: | | | | |
|---|---|---|---|---|---|
| | no act. subs.[1] | 1000 ppm AS III | 3 ppm AS I 1000 ppm AS III | 10 ppm AS I 1000 ppm AS III | 30 ppm AS I 1000 ppm AS III |
| 1 | 32 35 × $10^4$ 33 | — | 18 × $10^4$ | 8 × $10^2$ | 5 × $10^1$ |
| 2 | 31 — | 20 × $10^4$ | 17 | 22 | 7 |

-continued

| Taking of sample after ... minutes (duration of action) | no act. subs.[1] | 1000 ppm AS III | 3 ppm AS I 1000 ppm AS III | 10 ppm AS I 1000 ppm AS III | 30 ppm AS I 1000 ppm AS III |
|---|---|---|---|---|---|
| 3 | — | 18 | 71 × $10^3$ / 77 | 4 × $10^1$ / 2 | 2 × $10^1$ / 2 |
| 5 | — | 14 × $10^4$ / 16 | 19 × $10^3$ / 2 | 2 × $10^1$ / 0 | 0 |
| 7 | — | — | 11 × $10^1$ / 13 | 1 × $10^1$ / 0 | 0 |
| 10 | — | 14 × $10^4$ / 19 | 19 × $10^1$ / 12 | 0 | 0 |
| 15 | — | — | 14 × $10^1$ / 16 | 0 | 0 |
| 20 | — | 19 × $10^4$ / 20 | 1 × $10^1$ / 0 | 0 | 0 |
| 40 | — | 14 × $10^4$ / 25 | 0 | 0 | 0 |
| 60 | — | 20 × $10^4$ / 15 | 0 | 0 | 0 |
| 80 | — | 10 × $10^4$ / 19 | 0 | 0 | 0 |
| 120 | 24 / 26 × $10^4$ / 37 / 27 | 15 × $10^4$ / 11 | 0 | 0 | 0 |

[1]Control test with an 0.85% aqueous sodium chloride solution containing 1% of ethanol.

5-Chloro-2-(2,4-dichlorophenoxy)-phenol is, according to repeated tests, ineffective in the concentrations of 3 ppm and 10 ppm; an effect is indicated with 30 ppm, but does not become positively recognisable until the concentration reached 40 ppm. p-Chlorophenethyl alcohol alone is practically ineffective in the concentration of 1,000 ppm tested in the combination. Since the combination with 3 ppm of 5-chloro-2-(2,4-dichlorophenoxy)phenol already shows a positive action, the combination with a higher content of the stated phenol moreover acting rapidly or very rapidly, the synergism of the constituents used is in this case too clearly recognisable.

EXAMPLE 1

Hand disinfectant

In a mixture of 47.5 g of water and 35 g of glycerin are dissolved 10 g of sodium lauryl sulphate and then 1.0 g of 5-chloro-2-(2,4-dichlorophenoxy)-phenol and 1.0 g of phenethyl alcohol; to the solution are then added 5.0 g of partly ethoxylated, partly acetylated wool fat, e.g. Solulan 98 (protected trade-name of American Cholesterol Products Inc., Edison, N.J.), and, in order to obtain a physiologically favourable pH-value of 5.8 to 6.0, an amount of 0.5 g of citric acid.

It is also possible to use, instead of phenethyl alcohol, 1.0 g of p-chlorophenethyl alcohol.

EXAMPLE 2

Hand disinfectant

In the mixture of 25.0 g of isopropanol and 20 g of glycerol are dissolved 3.0 g of 5-chloro-2-(2,4-dichlorophenoxy)-phenol and 1.0 g of 2-phenoxyethanol. A mixture is then prepared separately of 8.0 g of N,N-bis-(2-hydroxyethyl)-laurinamide and 5.0 g of Solulan 98 (cp. Example 1) with 30 g of a 30% aqueous solution of sodium-N-lauroylsarcosinate. The two liquids are then mixed, and 0.5 g of citric acid in 7.5 g of water are added.

It is also possible to use, instead of 2-phenoxyethanol, 1.0 g of 2-(p-chlorophenoxy)-ethanol.

EXAMPLE 3

Ointment 5.0 g of polyoxyethylene stearate and 91.0 g of white soft paraffin are melted together; in the obtained melt are then dissolved 3.0 g of 5-chloro-2-(2,4-dichlorophenoxy)-phenol and 1.0 g of phenethyl alcohol.

Instead of 1.0 g of phenethyl alcohol, it is also possible to use 3.0 g together with 89.0 g of soft paraffin.

On the other hand, it is also possible to replace the phenethyl alcohol by 1.0 g of p-chlorophenethyl alcohol.

EXAMPLE 4

Ointment 10.0 g of wool fat and 86.0 g of white soft paraffin are melted together; in the obtained melt are then dissolved 3.0 g of 5-chloro-2-(2,4-dichlorophenoxy)-phenol and 1.0 g of 2-phenoxyethanol.

EXAMPLE 5

Cream

A mixture is prepared of 3.0 g of 5-chloro-2-(2,4-dichlorophenoxy)-phenol, 10.0 g of white soft paraffin (vaseline) and 10.0 g of emulsifying cetylstearyl alcohol (consisting of 9 parts of a mixture of alcohols and 1 part of the mixture of sodium cetyl sulphate and -stearyl sulphate), as well as 10.0 g of oleic acid decyl ester, and this is emulsified in the solution of 1.0 g of 2-phenoxyethanol in 25.0 g of 1,2-propanediol and 41.0 g of water.

Instead of 2-phenoxy ethanol, it is also possible to use 1.0 g of 2-(p-chlorophenoxy)-ethanol.

EXAMPLE 6

Cream 3.0 g of 5-chloro-2-(2,4-dichlorophenoxy)-phenol and 9.0 g of a 1:1-mixture of cetyl and stearyl alcohol are dissolved, with heating, in 15.0 g of paraffin oil. The obtained solution is emulsified in the solution of 1.0 g of phenethyl alcohol and 1.0 g of sodium lauryl sulphate in 71.0 g of water.

Instead of phenethyl alcohol, it is also possible to use 1.0 g of 2-phenoxyethanol.

EXAMPLE 7

Suspension

Into the mixture of 5.0 g of glycerin and 88.75 g of water are sprinkled 1.75 g of tragacanth and 0.50 g of hydroxyethyl cellulose, and allowed to swell. To the mixture are then added 3.00 g of 5-chloro-2-(2,4-dichlorophenoxy)-phenol and 1.0 g of phenethyl alcohol, and the thus obtained suspension is homogenised.

Instead of phenethyl alcohol, it is also possible to use 1.0 g of p-chlorophenethyl alcohol or 1.0 g of 2-phenoxyethanol.

EXAMPLE 8

Solution

In a mixture of 55.0 g of 1,2-propanediol and 10.0 g of ethanol are dissolved 3.0 g of 5-chloro-2-(2,4-dichlorophenoxy)-phenol and 1.0 g of 2-phenoxyethanol. In a separate operation, 1.0 g of hydroxyethyl cellulose is allowed to swell in 30.0 g of water, and the two solutions are mixed together.

Instead of 2-phenoxyethanol, it is also possible to use 1.0 g of 2-(p-chlorophenoxy)-ethanol.

EXAMPLE 9

Solution 3.0 g of 5-chloro-2-(2,4-dichlorophenoxy)-phenol and 3.0 g of phenethyl alcohol are dissolved in 94.0 g of polyethylene glycol (mean molecular weight 380–420).

Instead of phenethyl alcohol, it is also possible to use 1.0 g of p-chlorophenethyl alcohol together with 96.0 g of polyethylene glycol.

EXAMPLE 10

Wound powder 40.9 g of rice starch are impregnated with a mixture of 1.0 g of phenethyl alcohol and 1.0 g of ethanol. After the ethanol has been evaporated off, 3.0 g of 5-chloro-2-(2,4-dichlorophenoxy)-phenol, 5.0 g of zinc oxide, and 50.0 g of talcum impregnated with 0.1 g of perfume are added, and the whole thoroughly mixed. The mixture is then passed through a suitable fine sieve, and again well mixed.

Instead of the mixture of phenethyl alcohol and ethanol, it is also possible to use an ethanolic solution as concentrated as possible of 1.0 g of 2-phenoxyethanol, or of 1.0 g of p-chlorophenethyl alcohol.

What is claimed is:

1. A composition for the control of bacteria comprising antibacterially effective amounts of 5-chloro-2-(2,4-dichlorophenoxy)-phenol and phenethyl alcohol in a proportion within the range of 3 to 1 and 1 to 5.

2. A composition according to claim 1 comprising antibacterially effective amounts of 5-chloro-2-(2,4-dichlorophenoxy)-phenol and phenethyl alcohol in a proportion within the range of 3 to 1 and 1 to 5 and an inert carrier compatible therewith.

3. A composition according to claim 1 comprising 1 to 3% of 5-chloro-2-(2,4-dichlorophenoxy)-phenol and 1 to 5% of phenethyl alcohol and an inert carrier compatible therewith.

4. A method for combatting bacteria which comprises contacting said bacteria with an antibacterially effective amount of the composition according to claim 1.

* * * * *